(12) United States Patent
Tollin et al.

(10) Patent No.: US 10,131,611 B2
(45) Date of Patent: Nov. 20, 2018

(54) PROCESS FOR THE HYDRODECHLORINATION OF A FEED COMPRISING DICHLOROACETIC ACID

(71) Applicant: Akzo Nobel Chemicals International B.V., Arnhem (NL)

(72) Inventors: Lars Magnus Tollin, Skoghall (SE); Cornelis Kooijman, Deventer (NL)

(73) Assignee: Akzo Nobel Chemicals International B.V., Arnhem (NL)

( * ) Notice: Subject to any disclaimer, the term of this patent is extended or adjusted under 35 U.S.C. 154(b) by 0 days.

(21) Appl. No.: 15/579,892

(22) PCT Filed: Jun. 9, 2016

(86) PCT No.: PCT/EP2016/063102
§ 371 (c)(1),
(2) Date: Dec. 5, 2017

(87) PCT Pub. No.: WO2016/198495
PCT Pub. Date: Dec. 15, 2016

(65) Prior Publication Data
US 2018/0170852 A1 Jun. 21, 2018

(30) Foreign Application Priority Data
Jun. 12, 2015 (EP) .................................. 15171965

(51) Int. Cl.
*C07C 51/377* (2006.01)
(52) U.S. Cl.
CPC ................. *C07C 51/377* (2013.01)
(58) Field of Classification Search
CPC .................................................. C07C 51/377
See application file for complete search history.

(56) References Cited

U.S. PATENT DOCUMENTS

| 2,863,917 | A | 12/1958 | Rucker et al. |
| 3,739,023 | A | 6/1973 | Sennewald et al. |
| 3,754,029 | A | 8/1973 | Holtermann et al. |
| 4,051,019 | A | 9/1977 | Johnson |
| 4,159,785 | A | 7/1979 | Berry, Jr. |
| 5,191,118 | A | 3/1993 | Correia et al. |
| 5,356,850 | A | 10/1994 | Correia et al. |
| 5,449,501 | A | 9/1995 | Luebke et al. |
| 8,101,798 | B2* | 1/2012 | Timmermans ........ C07C 51/377 562/604 |

FOREIGN PATENT DOCUMENTS

| DE | 1 072 980 B | 1/1960 |
| DE | 1 816 931 A1 | 7/1970 |
| EP | 0 453 690 A1 | 10/1991 |
| EP | 0 557 169 A1 | 8/1993 |
| EP | 0 727 250 A2 | 8/1996 |
| EP | 0 769 462 A1 | 4/1997 |
| NL | 109769 C | 10/1964 |
| WO | 2008/025758 A1 | 3/2008 |
| WO | 2008/109671 A2 | 9/2008 |
| WO | 2013/057126 A1 | 4/2013 |
| WO | WO-2013057126 A1 * | 4/2013 ........... C07C 51/487 |

OTHER PUBLICATIONS

Shah, Y.T., "Gas-liquid-solid reactor design", McGraw-Hill Inc., 1979, p. 93.
Westerterp & Wammes (K. Roel Westerterp, Wino J.A. Wammes: "Three-Phase Trickle-Bed Reactors" in Ullmann's Encyclopedia of Industrial Chemistry, Wiley-VCH Verlag GmbH & Co. KGaA, weinheim, 2005, 34 pages.
Hofmann (Hans Hofmann, "Hydrodynamics and hydrodynamic models of fixed bed reactors" in Agostini Gianetto and Peter L. Silveston (eds.), Multiphase chemical reactors—theory, design, scale-up, Hemishere Publishing Co., 1986, 1 page.
Mary et al., "Trickle-Bed Laboratory Reactors for Kinetic Studies," International Journal of Chemical Reactor Engineering, vol. 7: R2, 2009, 70 pages.
Saroha & Nigam, "Trickle-bed reactors," Reviews in Chemical Engineering, 12, 3-4, 207-347, 1996.
Gert Griffioen and Michel Wijbrands, "Caring for Catalysts," Hydrocarbon Engineering, Jun. 2010.

* cited by examiner

*Primary Examiner* — Paul A Zucker
(74) *Attorney, Agent, or Firm* — McDonnell Boehnen Hulbert & Berghoff LLP

(57) ABSTRACT

The present invention is directed to a process for catalytic hydrodechlorination of dichloroacetic acid, wherein hydrogen gas is contacted with a liquid feed comprising dichloroacetic acid and monochloroacetic acid to form a product stream comprising monochloroacetic acid and an off gas stream comprising hydrogen chloride and hydrogen, and wherein the product stream is contacted with nitrogen gas so as to remove hydrogen gas present in the product stream.

21 Claims, No Drawings

PROCESS FOR THE HYDRODECHLORINATION OF A FEED COMPRISING DICHLOROACETIC ACID

This application is the U.S. national phase under 35 U.S.C. § 371 of international application PCT/EP/2016/063102, filed Jun. 9, 2016, which claims priority to European application EP 15171965.5, filed Jun. 12, 2015.

The present invention relates to a process for the hydrodechlorination of a feed comprising dichloroacetic acid (DCA).

The predominant industrial route for the production of monochloroacetic acid is by reacting acetic acid with chlorine. Such a process is commonly known and generally makes use of a reactor in which a mixture of liquid acetic acid (HAc) is reacted with chlorine under anhydrous conditions, using acetyl chloride as the catalyst. Acetyl chloride is preferably formed in-situ by the addition of e.g. acetic anhydride. In the chlorination reactor, monochloroacetic acid (MCA) and gaseous HCl are formed together with by-products of which dichloroacetic acid (DCA) and trichloroacetic acid (TCA) are examples.

After the MCA-containing reaction product mixture has passed the reactor(s) and the catalyst recovery section, DCA is present in a significant amount, typically about 3-10%. To reduce the amount of DCA in the MCA, the MCA/DCA-containing product mixture is subsequently subjected to a purification process. The purification process can either be a physical separation, such as crystallization or distillation, or a chemical conversion, such as a reduction where DCA is reduced with hydrogen in the presence of a hydrogenation catalyst, e.g. a metal-based catalyst.

As the boiling points of monochloroacetic acid and dichloroacetic acid are very close (189° and 194° C., respectively), removal of DCA from MCA by distillation is expensive and uneconomical.

With crystallization, the concentration of dichloroacetic acid in a crude monochloroacetic acid feed can only be reduced by a factor of approximately 4, i.e., for example, from 3 to 0.7-0.8% by weight, with a one-stage recrystallization. Hence, for the production of pure monochloroacetic acid, the space and time requirements are considerable. Furthermore, after several crystallizations, a mother liquor remains comprising a mixture of monochloroacetic acid and dichloroacetic acid. Although this mother liquor still comprises at least 30% by weight of monochloroacetic acid, depending on the cooling conditions, it cannot be converted into a saleable product by further crystallization and has to be regarded as waste.

It is known that the concentration of dichloroacetic acid in crude monochloroacetic acid can be reduced considerably by a catalytic hydrodechlorination (for example in accordance with U.S. Pat. Nos. 5,191,118 and 5,356,850).

This reaction can be carried out in the vapour phase (for example in accordance with NL 109,769 and DE 1,072,980). However, this vapour phase reaction requires the evaporation of the feed to the hydrodechlorination reactor, which is unattractive with respect to energy consumption and investment costs for required heat transfer equipment.

Alternatively, the hydrodechlorination is carried out in the liquid phase. In this case the MCA/DCA feed is in the liquid phase. Said liquid feed is contacted with hydrogen gas in the presence of a catalyst to form monochloroacetic acid and hydrogen chloride. The resulting product stream comprises monochloroactetic acid, while the off gas stream comprises hydrogen chloride and unreacted hydrogen gas.

Although the liquid process definitely has advantages over the process in the vapour phase, a drawback of the liquid process is the risk of minor amounts of hydrogen dissolving in the product stream. This may cause accumulation of hydrogen gas in the vacuum system of the downstream processing with the risk of explosion.

The object of the present invention is to provide a safe process for the purification of monochloracetic acid by the catalytic hydrodechlorination of dichloroacetic acid (and optionally trichloroacetic acid) in the liquid phase which may be conducted on industrial scale.

By an "industrial scale process" is meant that the catalytic hydrodechlorination step is carried out in an industrial scale sized vertical tubular reactor, hereinafter meaning a vertical tubular reactor having a diameter equal to or greater than 0.4 m.

To this end the present invention is directed to a process for catalytic hydrodechlorination of dichloroacetic acid, wherein hydrogen gas is contacted with a liquid feed comprising dichloroacetic acid and monochloroacetic acid to form a product stream comprising monochloroacetic acid and an off gas stream comprising hydrogen chloride and hydrogen, and wherein the product stream is contacted with nitrogen gas so as to remove hydrogen gas present in the product stream.

When contacting the liquid product stream with nitrogen gas, any hydrogen gas dissolved in the product stream will be taken up into the nitrogen gas. This may be accomplished by simply bubbling the nitrogen gas through the liquid product stream, but preferably the product stream is fed through a nitrogen gas stripper.

Stripping is a physical separation process where one or more components are removed from a liquid stream by a vapor stream. In industrial applications the liquid and vapor streams can have co-current or countercurrent flows. Stripping is usually carried out in either a packed or trayed column.

Stripping is mainly conducted in trayed towers (plate columns) and packed columns, and less often in spray towers, bubble columns, and centrifugal contactors.

Trayed towers consist of a vertical column with liquid flowing in the top and out the bottom. The vapor phase enters in the bottom of the column and exits out of the top. Inside of the column are trays or plates. These trays force the liquid to flow back and forth horizontally while the vapor bubbles up through holes in the trays. The purpose of these trays is to increase the amount of contact area between the liquid and vapor phases.

Packed columns are similar to trayed columns in that the liquid and vapor flows enter and exit in the same manner. The difference is that in packed towers there are no trays. Instead, packing is used to increase the contact area between the liquid and vapor phases. There are many different types of packing used and each one has advantages and disadvantages.

As mentioned previously, strippers can be trayed or packed. Packed columns, and particularly when random packing is used, are usually favored for smaller columns with a diameter less than 0.6 m and a packed height of not more than 6 m. Packed columns can also be advantageous for corrosive fluids, high foaming fluids, when fluid velocity is high, and when particularly low pressure drop is desired. Trayed strippers are advantageous because of ease of design and scale up. Structured packing can be used similar to trays despite possibly being the same material as dumped (random) packing. Using structured packing is a common method to increase the capacity for separation or to replace damaged trays.

Trayed strippers can have sieve, valve, or bubble cap trays while packed strippers can have either structured packing or random packing. Trays and packing are used to increase the contact area over which mass transfer can occur as mass transfer theory dictates. Packing can have varying material, surface area, flow area, and associated pressure drop. Older generation packing include ceramic Rachig rings and Berl saddles. More common packing materials are metal and plastic Pall rings, metal and plastic Zbigniew Biatecki rings, and ceramic Intalox saddles. Each packing material of this newer generation improves the surface area, the flow area, and/or the associated pressure drop across the packing. Also important, is the ability of the packing material to not stack on top of itself. If such stacking occurs, it drastically reduces the surface area of the material.

Conventional gas strippers may be used as nitrogen gas strippers. They are known in the art and need no further elucidation here.

As mentioned above, the hydrodechlorination takes place in the presence of a catalyst. Said catalyst may be finely dispersed in the liquid phase (for example in accordance with U.S. Pat. No. 2,863,917, DE 1,816,931 and WO 2008/025758). However to avoid the troublesome separation of the finely dispersed catalyst from the liquid phase, the high degree of backmixing, in case of continuous operation of these slurry reactors, the use of a reactor wherein the catalyst is accommodated in a fixed bed is preferred. A process for hydrodechlorination using a fixed bed is described in WO2013/057126.

When accommodating the catalyst in a fixed bed, preferably a heterogeneous catalyst is used for the hydrodechlorination.

It is further preferred to feed the liquid feed comprising dichloroacetic acid and monochloroacetic acid to the top of a vertical tubular reactor in which it trickles downwards over a heterogeneous catalyst that is accommodated in a fixed bed, while hydrogen is fed to the top or bottom of the vertical tubular reactor (for example in accordance with U.S. Pat. No. 3,754,029). These reactors are commonly known as trickle-bed reactors). In a vertical tubular reactor, a higher mass transfer rate can be achieved combined with a residence time distribution close to that of plug flow and wherein a higher conversion is achieved.

From a hydrodynamic point of view countercurrent flow of the hydrogen gas is disadvantageous, as it limits the capacity of the reactor column by flooding.

It is therefore preferred to feed the liquid feed comprising dichloroacetic acid and monochloroacetic acid to the top of a vertical tubular reactor, with cocurrent downflow of hydrogen.

This way of operation prevents the excessive use of energy for the evaporation of the liquid feed to the reactor column, circumvents the troublesome separation of finely dispersed catalyst in slurry reactors, and allows for a broader operating window in comparison with trickle-bed reactors operated with countercurrent flow of the hydrogen and above all, allows for a safe processing without the risk of explosion.

The design and scale-up of these trickle-bed reactors (also denoted throughout this specification as vertical tubular reactors) is very complex due to complicated hydrodynamics, as argued by e.g. Shah (Y.T. Shah, Gas-liquid-solid reactor design, McGraw-Hill Inc., 1979, p. 93), Westerterp & Wammes (K. Roel Westerterp, Wino J. A. Wammes: "Three-Phase Trickle-Bed Reactors" in *Ullmann's Encyclopedia of Industrial Chemistry*, Wiley-VCH Verlag GmbH & Co. KGaA, weinheim, 2005, and Hofmann (Hans Hofmann, "Hydrodynamics and hydrodynamic models of fixed bed reactors" in Agostini Gianetto and Peter L. Silveston (eds.), *Multiphase chemical reactors—theory, design, scale-up*, Hemishere Publishing Co., 1986). Moreover, it is impossible to operate a laboratory vertical tubular reactor and an industrial vertical tubular reactor simultaneously at the same liquid hourly space velocity (i.e. the amount of liquid fed to the reactor per hour and per unit volume of catalyst) and superficial mass velocity (i.e. the amount of liquid fed to the reactor per square meter cross-section), due to the large difference between the geometry of such units (see Mary et al., "Trickle-Bed Laboratory Reactors for Kinetic Studies," *International Journal of Chemical Reactor Engineering*, Vol. 7: R2, 2009).

Another object of the present invention is to provide an industrial scale process for the purification of monochloroacetic acid by the catalytic hydrodechlorination of dichloracetic acid (and optionally trichloroacetic acid) in a vertical tubular reactor while minimizing the required catalyst inventory.

The process according to the invention takes place in the presence of a catalyst. Suitable catalysts are solid heterogeneous hydrogenation catalysts comprising one or more metals of Group VIII of the Periodic Table of the Elements deposited on a carrier.

Preferably, the catalytic hydrodechlorination is carried out in a vertical tubular reactor, wherein the liquid feed is fed to the top of said vertical tubular reactor and wherein the hydrogen is fed to the top or bottom of the vertical tubular reactor and wherein the temperature in the top of the vertical tubular reactor is between 100 and 200° C., and wherein the pressure in the top of the vertical tubular reactor is between 0.2 and 1.0 MPa. More preferably a vertical tubular reactor is used with a diameter exceeding 0.4 m, with a solid heterogeneous hydrogenation catalyst being situated in a fixed catalyst bed.

More preferably the liquid feed is fed to the top of said vertical tubular reactor at a superficial mass velocity of between 1 and 10 kg/s per square meter of the horizontal cross-section of the vertical tubular reactor and a rate of between 250 and 3000 kg/hr per $m^3$ of said catalyst bed, the hydrogen is fed to the top or bottom of the vertical tubular reactor at a superficial gas velocity of between 0.025 to 0.25 $Nm^3$/s per square meter of the horizontal cross-section of the vertical tubular reactor, so as to obtain an average axial pressure gradient of at least 2 kPa per meter of said catalyst bed.

In a preferred embodiment, the liquid feed which is fed to the top of the vertical tubular reactor comprises at least 5.5% by weight of acetic acid. The acetic acid will partly evaporate in the trickle-bed reactor and thus increases the pressure drop over the reactor, resulting in a higher mass transfer coefficient.

The heterogeneous hydrogenation catalyst that is used in the process according to the present invention preferably comprises between 0.1 and 3% by weight, more preferably between 0.5 and 2% by weight, based on the total weight of the heterogeneous catalyst, of one or more metals of Group VIII of the Periodic Table of the Elements. Preferably, the heterogeneous catalyst comprises ruthenium, rhodium, palladium and/or platinum. More preferably, it comprises palladium, platinum, or a combination thereof. Most preferably, it comprises palladium (Pd) and either sulfur or a sulfur compound. For example, the catalyst described in EP 0557169 or the catalysts as described in EP 0453690 are suitable for use in the present process.

The carrier on which the one or more metals of Group VIII of the Periodic Table of the Elements have been deposited is preferably selected from the group consisting of activated carbon, silica, alumina, zirconium oxide, and titanium oxide. Activated carbon is most preferred. The carrier may comprise sulfur or sulfur-containing components (either organic or inorganic in nature).

In a preferred embodiment, the heterogeneous catalyst which is used in the process according to the present invention is palladium on an activated carbon carrier, while sulfur or sulfur-containing components such as $CS_2$ may be added to the feed.

In one embodiment, the one or more metals of the heterogeneous hydrogenation catalyst have been deposited on particles prepared from activated carbon, silica, or alumina, said particles being in the form of irregularly shaped granules, spheres, rings, trilobes, quadrulobes, or extrudates. More preferably, said particles are in the form of extrudates, trilobes, or quadrulobes, having a diameter of between 0.5 and 5 mm, preferably 0.8 to 3 mm, and a length of between 1 to 10 mm.

The catalyst is preferably situated in a fixed catalyst bed. This fixed bed can consist of one single bed, or may be subdivided into multiple sub-beds that are together called "the fixed catalyst bed". The catalyst bed or each sub-bed are supported by a support grid. Furthermore, a liquid distributor may be mounted above the surface of the entire catalyst bed and/or above the surface of one or more sub-beds to provide for a good liquid distribution over the diameter of said catalyst bed.

Suitable construction materials for these column internals (i.e. the support grid and the liquid distributor) include glass lined steel; tantalum and tantalum alloys, including tantalum claddings or coatings on steel or stainless steel; platinum and platinum alloys, including platinum claddings or coatings on steel or stainless steel; zirconium and zirconium alloys, including zirconium claddings or coatings on steel or stainless steel; graphite or impregnated graphite; ceramics-such as e.g. silicon carbide (SiC), zirconia ($ZrO_2$), alumina ($Al_2O_3$), glas, or quartz; acid resistant bricks; polytetrafluorethylene (PTFE); fluoropolymer—e.g. PTFE, perfluoralkoxy polymers (PFA), fluorinated ethylene-propylene (FEP) or polyethylenechlorotrifluoroethylene (ECTFE)—linings or coatings on steel, stainless steel, or fiber-reinforced plastics; nickel-chromium alloys; nickel-chromium-molybdenum alloys; nickel-copper alloys; silver, including silver claddings or silver coatings on steel or stainless steel; niobium and niobium alloys; and polyether ether ketone and PEEK-coated steel.

Preferred construction materials for the internals are glass lined steel; tantalum and tantalum alloys, including tantalum claddings or coatings on steel or stainless steel; platinum and platinum alloys, including platinum claddings or coatings on steel or stainless steel; zirconium and zirconium alloys, including zirconium claddings or coatings on steel or stainless steel; graphite or impregnated graphite; ceramics—such as silicon carbide (SiC), zirconia ($ZrO_2$), alumina ($Al_2O_3$), glass, or quartz; acid resistant bricks; polytetrafluorethylene (PTFE); fluoropolymer—e.g. PTFE, perfuloralkoxy polymers (PFA), fluorinated ethylene-propylene (FEP) or polyethylenechlorotrifluoroethylene (ECTFE)—linings or coatings on steel, stainless steel, or fiber-reinforced plastics.

More preferred construction material of the internals are glass lined steel; graphite or impregnated graphite; tantalum and tantalum alloys, including tantalum claddings or coatings on steel or stainless steel; and zirconium and zirconium alloys, including zirconium claddings or coatings on steel or stainless steel.

Most preferably, the construction material for the internals is graphite or impregnated graphite.

The hydrogen that is fed to the purification process according to the present invention is supplied by means of a source of hydrogen gas, which can either be substantially pure hydrogen gas or a gas comprising hydrogen gas and up to 50 mole % of nitrogen, hydrogen chloride, or a mixture thereof.

The hydrodechlorination is carried out using a vertical tubular reactor. Suitable reactor construction materials include glass lined steel; tantalum and tantalum alloys, including tantalum claddings or coatings on steel or stainless steel; platinum and platinum alloys, including platinum claddings or coatings on steel or stainless steel; zirconium and zirconium alloys, including zirconium claddings or coatings on steel or stainless steel; graphite or impregnated graphite; ceramics—e.g. silicon carbide (SiC), zirconia ($ZrO_2$), alumina ($Al_2O_3$), glas and quartz; acid resistant bricks, polytetrafluorethylene (PTFE); fluoropolymer—e.g. PTFE, perfuloralkoxy polymers (PFA), fluorinated ethylene-propylene (FEP) or polyethylenechlorotrifluoroethylene (ECTFE)—linings or coatings on steel, stainless steel, or fiber-reinforced plastics; nickel-chromium alloys; nickel-chromium-molybdenum alloys; nickel-copper alloys; silver, including silver claddings or silver coatings on steel or stainless steel; niobium and niobium alloys; and polyether ether ketone or PEEK coated steel.

Preferred construction materials are glass lined steel; tantalum and tantalum alloys, including tantalum claddings or coatings on steel or stainless steel; platinum and platinum alloys, including platinum claddings or coatings on steel or stainless steel; zirconium and zirconium alloys, including zirconium claddings or coatings on steel or stainless steel; graphite or impregnated graphite; ceramics—such as silicon carbide (SiC), zirconia ($ZrO_2$), alumina ($Al_2O_3$), glass and quartz; acid resistant bricks; polytetrafluorethylene (PTFE); fluoropolymer—e.g. PTFE, perfuloralkoxy polymers (PFA), fluorinated ethylene-propylene (FEP), or polyethylenechlorotrifluoroethylene (ECTFE)—linings or coatings on steel, stainless steel, or and fiber-reinforced plastics.

More preferably, the construction material is selected from the group consisting of glass lined steel; tantalum and tantalum alloys, including tantalum claddings or coatings on steel or stainless steel; and zirconium and zirconium alloys, including zirconium claddings or coatings on steel or stainless steel. The most preferred construction material is glass lined steel.

As mentioned above, the liquid feed is fed to the top of said vertical tubular reactor at a superficial mass velocity of between 1 and 10 kg/s per square meter of the horizontal cross-section of said reactor (the term superficial mass velocity ($kg/m^2/s$) refers to the mass flow divided by the horizontal cross-sectional area of said reactor). Preferably, it is fed to the top of said vertical tubular reactor at a superficial mass velocity of at least 2 kg/s per square meter of the horizontal cross-section of said reactor, more preferably at least 2.5 kg/s per square meter of the horizontal cross-section of said reactor, and most preferably at least 3 kg/s per square meter of the horizontal cross-section of said reactor. Preferably, the liquid feed is fed to the top of said vertical tubular reactor at a superficial mass velocity of at most 8 kg/s per square meter of the horizontal cross-section of said reactor, more preferably at a superficial mass velocity of at most 7 kg/s per square meter of the horizontal cross-section of said reactor, and most preferably at a superficial mass velocity of at most 6 kg/s per square meter of the horizontal cross-section of said reactor.

The hydrogen is fed to the top of the vertical tubular reactor at a superficial gas velocity of between 0.025 to 0.25 $Nm^3/s$ per square meter of the horizontal cross-section of the vertical tubular reactor (the term superficial gas velocity (m/s) refers to the gas velocity based on the horizontal cross-section of said vertical tubular reactor). Preferably, the hydrogen is fed to the top or bottom of the vertical tubular reactor at a superficial gas velocity of at least 0.03 $Nm^3/s$ per square meter of the horizontal cross-section of the vertical tubular reactor, more preferably at a superficial gas velocity of at least 0.035 $Nm^3/s$ per square meter of the horizontal cross-section of the vertical tubular reactor, and most preferably at a superficial gas velocity of at least 0.04 $Nm^3/s$ per square meter of the horizontal cross-section of the vertical tubular reactor. Preferably, it is fed at a superficial gas velocity of at most 0.25 $Nm^3/s$ per square meter of the horizontal cross-section of the vertical tubular reactor, more preferably of at most 0.20 $Nm^3/s$ per square meter of the horizontal cross-section of the vertical tubular reactor, and most preferably of at most 0.15 $Nm^3/s$ per square meter of the horizontal cross-section of the vertical tubular reactor.

The temperature in the top of the reactor is preferably kept between 100 and 200° C., and more preferably between 145 and 175° C. The pressure in the top of the vertical tubular reactor is preferably kept between 0.2 and 1.0 MPa, preferably between 0.3 and 0.6 MPa.

In order to minimize the risk of liquid maldistribution in the trickle-bed reactor (see e.g. Saroha & Nigam, "Trickle-bed reactors," *Reviews in Chemical Engineering*, 12, 3-4, 207-347, 1996), the fixed bed in which the heterogeneous hydrogenation catalyst is situated has preferably been prepared by loading the vertical tubular reactor with the heterogeneous hydrogenation catalyst using a dense loading technique. Maldistribution in catalyst beds is known to significantly decrease the reactor's performance and run-time. The dense loading technique is a conventional loading technique whereby the vertical tubular reactor is loaded with particles of catalyst simultaneously over the entire cross-section of said reactor. The result is that a catalyst bed is obtained which is uniformly loaded and wherein the density is increased when compared to other reactor loading techniques. When compared to sock loading, a well-known loading technique, the density of the catalyst bed has increased by on average at least 10%, as can be found in Gert Griffioen and Michel Wijbrands, "Caring for Catalysts," *Hydrocarbon Engineering*, June 2010. The fixed bed with densely loaded catalyst according to the present invention can for instance be prepared using the well-known Densicat® or the Catapac™ technique. Suitable dense loading methods and equipment are described in EP 769,462, U.S. Pat. Nos. 4,051,019, 4,159,785, EP 0727250, WO2008/109671, and U.S. Pat. No. 5,449,501.

The liquid feed to be subjected to the process according to the present invention preferably comprises
(i) between 60 and 99.5% by weight of monochloroacetic acid,
(ii) between 0.05 and 20% by weight, preferably between 1 and 12% by weight, of dichloroacetic acid,
(iii) between 0 and 30% by weight of acetic acid,
(iv) between 0.1 and 5% by weight of water, preferably between 0.1 and 1% by weight, most preferably between 0.1 and 0.5% by weight of water, and
(v) between 0 and 5% by weight of other components, up to a total of 100%, based on the total weight of the liquid feed.

Other components may include a minor amount of acid anhydrides, trichloroacetic acid, bromoacetic acid, and alpha-chloropropionic acid. It is noted that due to the presence of the water, acid chlorides cannot be present in said liquid feed.

The liquid feed to be subjected to the process according to the present invention preferably comprises at least 5.5% by weight of acetic acid, more preferably at least 6% by weight of acetic acid, and most preferably at least 8% by weight of acetic acid, based on the total weight of the liquid feed. Preferably, no more than 20% of acetic acid is present in the liquid feed, more preferably no more than 12% by weight of acetic acid is present in the liquid feed, based on the total weight of the liquid feed.

With the process according to the invention a product stream can be obtained having very low amounts of dichloroacetic acid. The resulting product stream comprises less than 1% by weight dichloroacetic acid, preferably less than 0.5% by weight, more preferably less than 0.1% by weight dichloroacetic acid, and most preferably less than 0.05% by weight dichloroacetic acid.

The process according to the present invention is further illustrated by the following non-limiting examples.

EXAMPLE 1

A liquid feed of 1,620 kg/h comprising 88.1% monochloroacetic acid, 4.1% dichloroacetic acid, 5.4% acetic acid, 1.9% HCl, and 0.5% water was mixed with 3.86 kg/h hydrogen. The resulting gas-liquid mixture was heated to 171° C. and fed to the top of a vertical column with a diameter of 0.8 m and a length of 16 m. The vertical column was filled with a catalyst comprising 1% of Pd on an activated carbon support (catalyst particles comparable to those described in Example 1 of EP 0557169). The catalyst particles were loaded into the reactor by first filling the reactor with water and (slowly) adding the catalyst. Where necessary, water was allowed to drain via the bottom of the reactor to prevent the reactor from overflowing during its filling with catalyst. The reactor is completely drained after all the required catalyst has been added. The catalyst particles were in the form of extrudates having a diameter of 1.5 mm and an average length over diameter ratio of 1.84. The pressure in the top of the column was maintained at 0.32 MPa. The pressure drop over the vertical column was 4 kPa. The gas flow from the bottom of the reactor was passed over a condenser and the condensed vapours were mixed with the liquid leaving the bottom of the reactor, resulting in a crude mixture comprising 0.19% dichloroacetic acid. The crude mixture was led through a nitrogen gas stripper. The final monochloroacetic acid product comprised 0.20% dichloroacetic acid, after distilling off the light and heavy ends.

EXAMPLE 2

A liquid feed of 1,620 kg/h comprising 88.1% monochloroacetic acid, 4.1% dichloroacetic acid, 5.4% acetic acid, 1.9% HCl, and 0.5% water was mixed with 3.86 kg/h hydrogen. The resulting gas-liquid mixture was heated to 171° C. and fed to the top of a vertical column with a diameter of 0.6 m and a length of 16 m, reducing the catalyst inventory from 8 $m^3$ to 4.5 $m^3$. The vertical column was filled with a catalyst comprising 1% of Pd on an activated carbon support (catalyst particles comparable to those described in Example 1 of EP 0557169). The catalyst particles were loaded into the reactor by first filling the reactor with water and (slowly) adding the catalyst. Where necessary, water was allowed to drain via the bottom of the reactor to prevent the reactor from overflowing during its filling with catalyst. The reactor is completely drained after all the required catalyst has been added. The catalyst particles were in the form of extrudates having a diameter of 1.5 mm and an average length over diameter ratio of 1.84. The pressure in the top of the column was maintained at 0.32 MPa. The pressure drop over the vertical column was 27 kPa. The gas flow from the bottom of the reactor was passed over a condenser and the condensed vapours were mixed with the liquid leaving the bottom of the reactor, resulting in a crude mixture comprising 0.11% dichloroacetic acid. The crude mixture was led through a nitrogen gas stripper. The final monochloroacetic acid product, after distilling off the light and heavy ends, comprised 0.11% dichloroacetic acid.

The results as shown in Example 1 and Example 2 clearly show that with less catalyst (in a column having a smaller diameter), a purer product is obtained.

EXAMPLE 3

A liquid feed of 1,620 kg/h comprising 88.1% monochloroacetic acid, 4.1% dichloroacetic acid, 8.5% acetic acid, 1.9% HCl, and 0.5% water was mixed with 3.86 kg/h hydrogen. The resulting gas-liquid mixture was heated to 171° C. and fed to the top of a vertical column with a diameter of 0.6 m and a length of 16 m. The vertical column was filled with a catalyst comprising 1% of Pd on an activated carbon support (catalyst particles comparable to those described in Example 1 of EP 0557169). The catalyst particles were loaded into the reactor by first filling the reactor with water and (slowly) adding the catalyst. Where necessary, water was allowed to drain via the bottom of the reactor to prevent the reactor from overflowing during its filling with catalyst. The reactor is completely drained after all the required catalyst has been added. The catalyst particles were in the form of extrudates having a diameter of 1.5 mm and an average length over diameter ratio of 1.84. The pressure in the top of the column was maintained at 0.32 MPa. The pressure drop over the vertical column was 32 kPa. The gas flow from the bottom of the reactor was passed over a condenser and the condensed vapours were mixed with the liquid leaving the bottom of the reactor, resulting in a crude mixture comprising 0.083% dichloroacetic acid. The crude mixture was led through a nitrogen gas stripper. The final monochloroacetic acid product, after distilling off the light and heavy ends, comprised 0.093% dichloroacetic acid.

This Example shows that with an increased acetic acid content in the feed and as a result thereof a higher average axial pressure gradient, an even purer product is obtained.

EXAMPLE 4

A liquid feed of 1,620 kg/h comprising 85% monochloroacetic acid, 4.1% dichloroacetic acid, 8.5% acetic acid, 1.9% HCl, and 0.5% water was mixed with 3.86 kg/h hydrogen. The resulting gas-liquid mixture was heated to 171° C. and fed to the top of a vertical column with a diameter of 0.6 m and a length of 16 m. The vertical column was filled with a catalyst comprising 1% of Pd on an activated carbon support (catalyst particles comparable to those described in Example 1 of EP 0557169). The reactor was filled with catalyst by means of the Densicat® dense loading technique. Other dense loading techniques, including e.g. the Catapac™ dense loading technique, are also suitable. The catalyst particles were in the form of extrudates having a diameter of 1.5 mm and an average length over diameter ratio of 1.84. The pressure in the top of the column was maintained at 0.32 MPa. The pressure drop over the vertical column was 137 kPa. The gas flow from the bottom of the reactor was passed over a condenser and the condensed vapours were mixed with the liquid leaving the bottom of the reactor, resulting in a crude mixture comprising 0.008% dichloroacetic acid. The crude mixture was led through a nitrogen gas stripper. The final monochloroacetic acid product, after distilling off the light and heavy ends, comprised 0.008% dichloroacetic acid.

Example 4 shows that when the catalyst was loaded using a dense loading technique (resulting in an even higher average axial pressure gradient), an even purer product is obtained.

EXAMPLE 5

The above mentioned example was repeated. Only in this case the acetic acid level in the feed was reduced to 0.5%, resulting in a liquid feed of 1,620 kg/h comprising 93% monochloroacetic acid, 4.1% dichloroacetic acid, 0.5% acetic acid, 1.9% HCl, and 0.5% water was mixed with 3.86 kg/h hydrogen. The resulting gas-liquid mixture was heated to 171° C. and fed to the top of a vertical column with a diameter of 0.6 m and a length of 16 m. The vertical column was filled with a catalyst comprising 1% of Pd on an activated carbon support (catalyst particles comparable to those described in Example 1 of EP 0557169). The reactor was filled with catalyst by means of the Densicat® dense loading technique. Other dense loading techniques, including e.g. the Catapac™ dense loading technique, are also suitable. The catalyst particles were in the form of extrudates having a diameter of 1.5 mm and an average length over diameter ratio of 1.84. The pressure in the top of the column was maintained at 0.32 MPa. The pressure drop over the vertical column was 88 kPa. The gas flow from the bottom of the reactor was passed over a condenser and the condensed vapours were mixed with the liquid leaving the bottom of the reactor, resulting in a crude mixture comprising 0.006% dichloroacetic acid. The crude mixture was led through a nitrogen gas stripper. The final monochloroacetic acid product, after distilling off the light and heavy ends, comprised 0.006% dichloroacetic acid.

EXAMPLE 6

A liquid feed of 4,043 kg/h comprising 88.1% monochloroacetic acid, 4.1% dichloroacetic acid, 5.4% acetic acid, 1.9% HCl, and 0.5% water was mixed with 8.91 kg/h hydrogen. The resulting gas-liquid mixture was heated to 171° C. and fed to the top of a vertical column with a diameter of 0.8 m and a length of 16 m. The vertical column was filled with a catalyst comprising 1% of Pd on an activated carbon support (catalyst particles comparable to those described in Example 1 of EP 0557169). The catalyst particles were loaded into the reactor by first filling the reactor with water and (slowly) adding the catalyst. Where necessary, water was allowed to drain via the bottom of the reactor to prevent the reactor from overflowing during its filling with catalyst. The reactor is completely drained after all the required catalyst has been added. The catalyst particles were in the form of extrudates having a diameter of 1.5 mm and an average length over diameter ratio of 1.84. The pressure in the top of the column was maintained at 0.4 MPa.

The pressure drop over the vertical column was 31 kPa. The gas flow from the bottom of the reactor was passed over a condenser and the condensed vapours were mixed with the liquid leaving the bottom of the reactor, resulting in a crude mixture comprising 0.074% dichloroacetic acid. The crude mixture was led through a nitrogen gas stripper. The final monochloroacetic acid product comprised 0.080% dichloroacetic acid, after distilling off the light and heavy ends.

EXAMPLE 7

A liquid feed of 4,043 kg/h comprising 87.0% monochloroacetic acid, 4.1% dichloroacetic acid, 6.5% acetic acid, 1.9% HCl, and 0.5% water was mixed with 8.91 kg/h hydrogen. The resulting gas-liquid mixture was heated to 171° C. and fed to the top of a vertical column with a diameter of 0.8 m and a length of 16 m. The vertical column was filled with a catalyst comprising 1% of Pd on an activated carbon support (catalyst particles comparable to those described in Example 1 of EP 0557169). The catalyst particles were loaded into the reactor by first filling the reactor with water and (slowly) adding the catalyst. Where necessary, water was allowed to drain via the bottom of the reactor to prevent the reactor from overflowing during its filling with catalyst. The reactor is completely drained after all the required catalyst has been added. The catalyst particles were in the form of extrudates having a diameter of 1.5 mm and an average length over diameter ratio of 1.84. The pressure in the top of the column was maintained at 0.4 MPa. The pressure drop over the vertical column was 33 kPa. The gas flow from the bottom of the reactor was passed over a condenser and the condensed vapours were mixed with the liquid leaving the bottom of the reactor, resulting in a crude mixture comprising 0.068% dichloroacetic acid. The crude mixture was led through a nitrogen gas stripper. The final monochloroacetic acid product comprised 0.074% dichloroacetic acid, after distilling off the light and heavy ends.

The results as shown in Example 6 and Example 7 again show that with an increased acetic acid content in the feed, an even purer product is obtained.

EXAMPLE 8

A liquid feed of 4,043 kg/h comprising 87.0% monochloroacetic acid, 4.1% dichloroacetic acid, 6.5% acetic acid, 1.9% HCl, and 0.5% water was mixed with 8.91 kg/h hydrogen. The resulting gas-liquid mixture was heated to 171° C. and fed to the top of a vertical column with a diameter of 0.6 m and a length of 20 m. The vertical column was filled with a catalyst comprising 1% of Pd on an activated carbon support (catalyst particles comparable to those described in Example 1 of EP 0557169). The catalyst particles were loaded into the reactor by first filling the reactor with water and (slowly) adding the catalyst. Where necessary, water was allowed to drain via the bottom of the reactor to prevent the reactor from overflowing during its filling with catalyst. The reactor is completely drained after all the required catalyst has been added. The catalyst particles were in the form of extrudates having a diameter of 1.5 mm and an average length over diameter ratio of 1.84. The pressure in the top of the column was maintained at 0.4 MPa. The pressure drop over the vertical column was 165 kPa. The gas flow from the bottom of the reactor was passed over a condenser and the condensed vapours were mixed with the liquid leaving the bottom of the reactor, resulting in a crude mixture comprising 0.041% dichloroacetic acid. The crude mixture was led through a nitrogen gas stripper. The final monochloroacetic acid product comprised 0.046% dichloroacetic acid, after distilling off the light and heavy ends.

The results as shown in Example 7 and Example 8 show that with less catalyst (in a column with a smaller diameter), an even purer product is obtained.

EXAMPLE 9

The above mentioned example was repeated. Only in this case the acetic acid level in the feed was reduced to 0.5%, resulting in a liquid feed of 4,043 kg/h comprising 93.0% monochloroacetic acid, 4.1% dichloroacetic acid, 0.5% acetic acid, 1.9% HCl, and 0.5% water was mixed with 8.91 kg/h hydrogen. The resulting gas-liquid mixture was heated to 171° C. and fed to the top of a vertical column with a diameter of 0.6 m and a length of 20 m. The vertical column was filled with a catalyst comprising 1% of Pd on an activated carbon support (catalyst particles comparable to those described in Example 1 of EP 0557169). The catalyst particles were loaded into the reactor by first filling the reactor with water and (slowly) adding the catalyst. Where necessary, water was allowed to drain via the bottom of the reactor to prevent the reactor from overflowing during its filling with catalyst. The reactor is completely drained after all the required catalyst has been added. The catalyst particles were in the form of extrudates having a diameter of 1.5 mm and an average length over diameter ratio of 1.84. The pressure in the top of the column was maintained at 0.4 MPa. The pressure drop over the vertical column was 125 kPa. The gas flow from the bottom of the reactor was passed over a condenser and the condensed vapours were mixed with the liquid leaving the bottom of the reactor, resulting in a crude mixture comprising 0.037% dichloroacetic acid. The crude mixture was led through a nitrogen gas stripper. The final monochloroacetic acid product comprised 0.038% dichloroacetic acid, after distilling off the light and heavy ends.

This example shows that with much lower acetic acid content in the feed, also a pure product can be obtained. Due to the low amount of acetic acid in the feed, less heat of evaporation is needed, giving a higher temperature in the hydrogenation reactor, which increases the reaction rate, improving the DCA conversion.

EXAMPLE 10

A liquid feed of 4,043 kg/h comprising 87.0% monochloroacetic acid, 4.1% dichloroacetic acid, 6.5% acetic acid, 1.9% HCl, and 0.5% water was mixed with 8.91 kg/h hydrogen. The resulting gas-liquid mixture was heated to 171° C. and fed to the top of a vertical column with a diameter of 0.8 m and a length of 12 m. The vertical column was filled with a catalyst comprising 1% of Pd on an activated carbon support (catalyst particles comparable to those described in Example 1 of EP 0557169). The reactor was filled with catalyst by means of the Densicat® dense loading technique. Other dense loading techniques, including e.g. the Catapac™ dense loading techniques, are also suitable. The catalyst particles werein the form of extrudates having a diameter of 1.5 mm and an average length over diameter ratio of 1.84. The pressure in the top of the column was maintained at 0.4 MPa. The pressure drop over the vertical column was 97 kPa. The gas flow from the bottom of the reactor was passed over a condenser and the condensed vapours were mixed with the liquid leaving the bottom of the reactor, resulting in a crude mixture comprising 0.027% dichloroacetic acid. The crude mixture was led through a nitrogen gas stripper. The final monochloroacetic acid product comprised 0.030% dichloroacetic acid, after distilling off the light and heavy ends.

The difference between Examples 6, 7, 8 and Example 10 is that in Example 10, the catalyst was loaded using a dense loading technique and a high average axial pressure gradient was applied. This results in a pure product.

The invention claimed is:

1. A process for catalytic hydrodechlorination of dichloroacetic acid, wherein hydrogen gas is contacted with a liquid feed comprising dichloroacetic acid and monochloroacetic acid in the presence of a catalyst to form a product stream comprising monochloroacetic acid and an off gas stream comprising hydrogen chloride and hydrogen, and wherein the product stream is contacted with nitrogen gas so as to remove hydrogen gas present in the product stream, wherein hydrodechlorination takes place in a vertical tubular reactor.

2. The process according to claim 1 wherein the product stream is contacted with nitrogen gas by feeding the product stream through a nitrogen gas stripper.

3. The process according to claim 1 wherein the hydrogen gas that is contacted with the liquid feed is supplied by means of a source of hydrogen gas, which can either be pure hydrogen gas or a gas comprising hydrogen gas and up to 50 mole % of nitrogen, hydrogen chloride, or a mixture thereof.

4. The process according to claim 1 wherein the catalyst is situated in a fixed catalyst bed.

5. The process according to claim 4 wherein the fixed catalyst bed has been prepared by loading the vertical tubular reactor with the catalyst using a dense loading technique.

6. The process according to claim 1 wherein a heterogeneous precious metal catalyst on an inert carrier is used for the hydrodechlorination.

7. The process according to claim 1 wherein the liquid feed comprising dichloroacetic acid and monochloroacetic acid is fed to the top of a vertical tubular reactor, in which it trickles down over a heterogeneous catalyst that is accommodated in a fixed catalyst bed, with concurrent downflow of hydrogen.

8. The process according to claim 1 wherein the catalyst is a solid heterogeneous hydrogenation catalysts comprising one or more metals of Group VIII of the Periodic Table of the Elements deposited on a carrier.

9. The process according to claim 1 wherein the liquid feed comprising dichloroacetic acid and monochloroacetic acid is fed to the top of said vertical tubular reactor and wherein the hydrogen is fed to the top or bottom of the vertical tubular reactor and wherein the temperature in the top of the vertical tubular reactor is between 100 and 200° C., and wherein the pressure in the top of the vertical tubular reactor is between 0.2 and 1.0 MPa.

10. The process according to claim 4 wherein the liquid feed comprising dichloroacetic acid and monochloroacetic acid is fed to the top of said vertical tubular reactor at a superficial mass velocity of between 1 and 10 kg/s per square meter of the horizontal cross-section of the vertical tubular reactor and a rate of between 250 and 3000 kg/hr per $m^3$ of said fixed catalyst bed, the hydrogen is fed to the top or bottom of the vertical tubular reactor at a superficial gas velocity of between 0.025 to 0.25 $Nm^3/s$ per square meter of the horizontal cross-section of the vertical tubular reactor, so as to obtain an average axial pressure gradient of at least 2 kPa per meter of said catalyst bed.

11. The process according to claim 1 wherein the catalytic hydrodechlorination step is carried out in a vertical tubular reactor with a diameter exceeding 0.4 m.

12. The process according to claim 1 wherein the liquid feed comprising dichloroacetic acid and monochloroacetic acid which is fed to the top of the vertical tubular reactor comprises at least 5.5% by weight of acetic acid.

13. The process according to claim 1 wherein the liquid feed comprising dichloroacetic acid and monochloroacetic acid to be subjected to the process according to the present invention comprises
   (i) between 60 and 99.5% by weight of monochloroacetic acid,
   (ii) between 0.05 and 20% by weight of dichloroacetic acid,
   (iii) between 0 and 30% by weight of acetic acid,
   (iv) between 0.1 and 5% by weight of water and
   (v) between 0 and 5% by weight of other components, up to a total of 100%, based on the total weight of the liquid feed.

14. The process according to claim 1 wherein the resulting product stream comprises less than 1% by weight dichloroacetic acid.

15. The process according to claim 13 wherein the dichloroacetic acid is between 1 and 12% by weight of the liquid feed.

16. The process according to claim 13 wherein the water is between 0.1% and 1% by weight of the liquid feed.

17. The process according to claim 13 wherein the water is between 0.1% and 0.5% by weight of the liquid feed.

18. The process according to claim 14, wherein the resulting product stream comprises less than 0.5% by weight dichloroacetic acid.

19. The process according to claim 14, wherein the resulting product stream comprises less than 0.1% by weight dichloroacetic acid.

20. The process according to claim 14, wherein the resulting product stream comprises less than 0.05% by weight dichloroacetic acid.

21. The process according to claim 1, wherein the catalyst is a palladium catalyst.

* * * * *